United States Patent [19]

Orr et al.

[11] Patent Number: 4,976,953

[45] Date of Patent: Dec. 11, 1990

[54] SKIN CONDITIONING/CLEANSING COMPOSITIONS CONTAINING PROPOXYLATED GLYCEROL DERIVATIVES

[75] Inventors: Thomas V. Orr, Cincinnati; Anthony D. Sabatelli, Hamilton, both of Ohio

[73] Assignee: The Procter & Gamble Company, Cincinnati, Ohio

[21] Appl. No.: 23,059

[22] Filed: Mar. 6, 1987

[51] Int. Cl.$^5$ .............................................. A61K 7/00
[52] U.S. Cl. .............................. 424/47; 252/DIG. 5
[58] Field of Search .................... 424/47; 252/DIG. 5

[56] References Cited

U.S. PATENT DOCUMENTS

| | | | |
|---|---|---|---|
| 2,839,419 | 6/1958 | Windover et al. | 106/188 |
| 2,949,402 | 8/1960 | Mehrabi-Nejad et al. | 167/82 |
| 3,395,215 | 7/1968 | Schubert | 424/47 |
| 3,427,248 | 2/1969 | Lamberti et al. | 252/117 |
| 4,246,285 | 1/1981 | Van Duzee | 424/47 |
| 4,478,853 | 10/1984 | Chaussee | 424/47 |

FOREIGN PATENT DOCUMENTS

| | | |
|---|---|---|
| 141253 | 5/1985 | European Pat. Off. . |
| 115823 | 4/1979 | Japan . |
| 2176481A | 12/1986 | United Kingdom . |

OTHER PUBLICATIONS

Stallberg, "Syntheses of Substituted Glycerol Ethers", *Chemica Scripta*, 7(1) 31–42 (1975).

Sagarin and Balsam *Cosmetics, Science and Technology*, 2nd Edition, vol. 1, pp. 32–35 (1972).

*Primary Examiner*—Patrick Ryan
*Attorney, Agent, or Firm*—Milton B. Graff, IV; Steven J. Goldstein; Jack D. Schaeffer

[57] ABSTRACT

Skin conditioning/cleansing compositions containing specific propoxylated glycerol derivatives are disclosed. These compositions possess both excellent skin conditioning and aesthetic properties.

15 Claims, No Drawings

SKIN CONDITIONING/CLEANSING COMPOSITIONS CONTAINING PROPOXYLATED GLYCEROL DERIVATIVES

TECHNICAL FIELD

The present invention relates to improved skin conditioning and/or cleansing compositions. Specifically, it relates to skin conditioning compositions and soap compositions containing propoxylated glycerol derivatives which are effective skin conditioning agents and also possess good aesthetics (i.e., they do not feel greasy or tacky).

BACKGROUND OF THE INVENTION

The treatment of human skin with various agents has been undertaken for many years with the goal being to keep the skin in a smooth and supple condition. Skin has the tendency to dry out when exposed to low humidity or to harsh detergent solutions for extended periods of time. From a physiological standpoint, dryness is a measure of the water content of the skin. Under normal conditions, the water content and vapor pressure of the epidermis are higher than those of the surrounding air with consequent evaporation of water from the skin surface. Skin becomes dry because of excessive loss of water from its surface which results in loss of water from the stratum corneum. Low humidity speeds up this process, exacerbating the drying of skin.

Continuous and prolonged immersion in soap or detergent solutions may contribute to dryness of the stratum corneum. The reason for this is that the surfactant medium promotes dissolution of the skin surface lipids, the horny layer lipids, and the dissolution of the hygroscopic water-soluble components in the corneum layer.

In attempts to alleviate or prevent the aforementioned conditions, many different emollient materials have been suggested for topical application to the skin. See, for example, Sagarin, *Cosmetics, Science and Technology*, 2nd Edition, Vol. 1, pages 34–36 (1972). The emollient materials are believed to increase the state of hydration of the corneous layer of the skin by altering the rate of diffusion of water from the lower epidermal and dermal layers, the rate of evaporation of water from the skin's surface, and the ability of the corneum layer to hold moisture.

Numerous other references disclose materials which are purported to be effective skin conditioners. However, the most effective and widely-used materials, such as glycerol, suffer from negative aesthetic qualities (e.g., greasiness or stickiness). Conversely, materials with better aesthetics tend to be ineffective skin conditioners. Therefore, the need exists for materials which can meet both efficacy and aesthetic criteria. Such materials would find immediate application, for example, in a facial moisturizer product where aesthetic properties are extremely important.

It is an object of the present invention to provide specific propoxylated glycerol derivatives which possess both excellent skin conditioning and aesthetic properties.

It is an object of the present invention to provide skin conditioning compositions, containing these propoxylated glycerol derivatives, which possess both excellent skin conditioning and aesthetic properties.

It is another object of this invention to provide skin cleansing compositions containing these propoxylated glycerol derivatives, which are effective skin cleansers and are also highly effective skin conditioners.

It is a further object of the present invention to provide methods for effective conditioning/cleansing of the skin.

These and other objects will become apparent from the description to follow.

As used herein, all parts, percentages and ratios are by weight unless otherwise indicated.

BACKGROUND ART

The use of glycerol as a constituent of cosmetic preparations is well known. See e.g., U.S. Pat. No. 4,421,769, Dixon and Kelm, issued Dec. 20, 1983. See also a series of articles by F. V. Wells, appearing in *Journal of the Society of Cosmetic Chemists*, Vol. IX, No. 1, pp. 19–25 and the following issues of *Soap, Perfumery and Cosmetics*: Feb., 1957, pp. 194–196, 218; Mar., 1957, pp. 291–294; June, 1957, pp. 605–608; Aug., 1957, pp. 817–820; and Feb., 1958, pp. 149–154. In fact, many commercially available skin lotions contain glycerol (e.g., The Procter & Gamble Company's WONDRA).

Similarly, the use of other polyhydric alcohols and polyether derivatives as emollient materials in topical compositions, is generally disclosed in the art. See, for example, Sagarin, *Cosmetics, Science and Technology*, 2nd Edition, Vol. 1, page 35 (1972). However, none of these references disclose or suggest skin conditioning compositions or soap compositions which contain the propoxylated glycerol derivatives of the present invention or the benefits associated therewith.

In fact, the art does not specifically disclose the propoxylated glycerol derivatives of the present invention. U.S. Pat. No. 2,839,419, Windover et al., issued June 17, 1958, discloses water soluble cellulose ether compositions. Specifically disclosed as plasticizers in these compositions are glycerol 2-hydroxyalkyl ethers, obtained by reacting 1 mole of glycerol with more than 3 moles of propylene oxide in an aqueous NaOH solution. U.S. Pat. No. 2,949,402, Mehrabi-Nejad et al., issued Aug. 16, 1960, discloses a composition useful for coating pharmaceutical tablets. One of the coating materials disclosed is hydroxypropylglycerol, made by reacting glycerin and propylene oxide so that the reaction product has an available hydroxypropyl substitution of about 2.5. None of these references disclose or suggest that the reaction products may be used in skin conditioning and cleansing compositions or that their topical use would provide any skin conditioning benefits.

SUMMARY OF THE INVENTION

There is provided compositions for cleansing and/or conditioning the skin containing specific propoxylated glycerol derivatives. The propoxylated glycerol derivatives are represented by the following formulas:

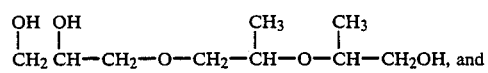

-continued $$\underset{\substack{|\phantom{OH}|\phantom{OH}|\phantom{CH_3}|\phantom{CH_3}\\CH_2-CH-CH_2-O-CH-CH_2-O-CH_2-CH-OH}}{OH\quad OH\quad\quad CH_3\quad\quad CH_3}$$

wherein n=1 or 2, and mixtures thereof. The compositions for conditioning the skin comprise: (a) from about 1% to about 60% by weight of the above-described propoxylated glycerol derivatives; and (b) a cosmetically-acceptable topical carrier.

The compositions for cleansing the skin comprise: (a) from about 1% to about 90% by weight of a cosmetically-acceptable surfactant selected from the group consisting of anionic, nonionic, zwitterionic, amphoteric and ampholytic surfactants and mixtures thereof, and (b) from about 1% to about 60% by weigth of the above-described propoxylated glycerol derivatives.

DETAILED DESCRIPTION OF THE INVENTION

The components of the present invention are described in detail below.

Propoxylated Glycerol Derivatives

All of the compositions of the present invention contain, as an essential component, a propoxylated glycerol derivative represented by the following formulas:

$$\underset{CH_2-CH-CH_2(OCH_2-CH)_nOH,}{OH\quad OH\quad\quad CH_3}$$

$$\underset{CH_2-CH-CH_2(OCH-CH_2)_nOH,}{OH\quad OH\quad CH_3}$$

$$\underset{CH_2-CH-CH_2-O-CH_2-CH-O-CH-CH_2OH,}{OH\quad OH\quad\quad CH_3\quad CH_3}\text{ and}$$

$$\underset{CH_2-CH-CH_2-O-CH-CH_2-O-CH_2-CH-OH}{OH\quad OH\quad\quad CH_3\quad\quad CH_3}$$

wherein n=1 or 2, and mixtures thereof. Preferred propoxylated glycerol derivatives are those where n=1.

The skin conditioning compositions of the present invention contain from about 1% to about 60%, preferably from about 2% to about 25%, of these propoxylated glycerol derivatives. The skin cleansing compositions of the present invention contain from about 1% to about 60%, preferably from about 2% to about 40%, of the propoxylated glycerol derivatives.

The propoxylated glycerol derivatives of the present invention can be synthesized, for example, by reacting the terminal hydroxy group of a suitably protected glycerol molecule (e.g., solketal) with propylene oxide, and then removing the acetonide protecting group as outlined in the following procedure.

$$\begin{array}{c}CH_3\diagdown_C\diagup CH_3\\O\phantom{xx}O\phantom{xxx}OH\\|\phantom{xxx}|\phantom{xxxx}|\\CH_2\text{---}CH\text{---}CH_2\end{array}\xrightarrow[\substack{(2)\ CH_2\text{---}CH\\\phantom{xxxxx}\diagdown O\diagup\phantom{x}|\\\phantom{xxxxxxxxx}CH_3}]{(1)\text{ Base}}$$

-continued $$\begin{array}{c}CH_3\diagdown_C\diagup CH_3\\O\phantom{xx}O\phantom{xxxx}CH_3\\|\phantom{xxx}|\phantom{xxxxx}|\\CH_2\text{-------}CH\text{---}CH_2(OCH_2\text{---}CH)_nOH\end{array}$$

and $$\begin{array}{c}CH_3\diagdown_C\diagup CH_3\\O\phantom{xx}O\phantom{xxxx}CH_3\\|\phantom{xxx}|\phantom{xxxxx}|\\CH_2\text{-------}CH\text{---}CH_2(OCH\text{---}CH_2)_nOH\end{array}\xrightarrow{H^+}$$

$$\underset{CH_2-CH-CH_2(OCH_2-CH)_nOH}{OH\quad OH\quad\quad CH_3}\text{ and}$$

$$\underset{CH_2-CH-CH_2(OCH-CH_2)_nOH}{OH\quad OH\quad CH_3}$$

The degree of propoxylation of the protected glycerol molecule is controlled by the amount of propylene oxide employed and its addition rate. Only the propoxylated glycerol derivatives wherein n=1 or 2 demonstrate the requisite skin conditioning efficacy and aesthetics, with $$\underset{CH_2-CH-CH_2-O-CH_2-CH-OH}{OH\quad OH\quad\quad CH_3}\text{ and}$$

$$\underset{CH_2-CH-CH_2-O-CH-CH_2-OH}{OH\quad OH\quad CH_3}$$

(i.e., n=1) being the preferred compounds.

Without being bound by theory, it is believed that the glycerol portion of these derivatives provide the skin conditioning benefits, whereas the more hydrophobic portion, derived from the propylene oxide, improves the aesthetic qualities (i.e., the compositions do not feel greasy or sticky).

Skin Conditioning Compositions

The skin conditioning compositions of the present invention contain as an essential component, from about 1% to about 60% of the propoxylated glycerol derivatives and a cosmetically acceptable topical carrier.

As used herein, "cosmetically-acceptable topical carrier" refers to a carrier capable of delivering the propoxylated glycerol derivatives to the skin without undue toxicity, irritation, allergic response, and the like. In addition, to be cosmetically-acceptable, the topical carrier must possess good cosmetic properties (e.g., feel, rub-in, lack of excessive greasiness and/or carriers are known and may be used herein. Generally, the topical carriers are organic in nature and are capable of having dispersed or dissolved therein the propoxylated glycerol derivatives. Sagarin, *Cosmetics, Science and Technology*, 2nd Edition, Vol. 1, pp. 48-65 (1972), incorporated herein by reference, contains numerous examples of suitable cosmetically-acceptable topical carriers. Examples of cosmetically-acceptable topical carriers include the various emollients, emulsifiers, and solvents (including water) described below.

The physical form of the skin conditioning compositions is not critical. The compositions can, for example, be formulated as lotions, creams, solutions, gels or solids.

A. Skin Conditioning Lotions

Skin conditioning lotions contain from about 1% to about 60%, preferably from about 5% to about 25%, of the propoxylated glycerol derivatives; from about 1% to about 20%, preferably from about 5% to about 10%, of an emollient; and the balance water, preferably from about 50% to about 90%.

As used herein, "emollients" refer to materials used for the prevention or relief of dryness, as well as for the protection of the skin. A wide variety of suitable emollients are known and used herein. Sagarin, *Cosmetics, Science and Technology*, 2nd Edition, Vol. 1, pp. 32-43 (1972), incorporated herein by reference, contains numerous examples of suitable materials. Examples of classes of emollients include the following:

1. Hydrocarbon oils and waxes. Examples include mineral oil, petrolatum, parrafin, ceresin, ozokerite, microcrystalline wax, polyethylene, and perhydrosqualene.

2. Silicone oils, such as dimethyl polysiloxanes, methylphenyl polysiloxanes, water-soluble and alcohol-soluble silicone glycol copolymers.

3. Triglyceride esters, for example vegetable and animal fats and oils. Examples include castor oil, safflower oil, cottonseed oil, corn oil, olive oil, cod liver oil, almond oil, avocado oil, palm oil, sesame oil, and soybean oil.

4. Acetoglyceride esters, such as acetylated monoglycerides.

5. Ethoxylated glycerides, such as ethoxylated glyceryl monostearate.

6. Alkyl esters of fatty acids having 10 to 20 carbon atoms. Methyl, isopropyl, and butyl esters of fatty acids are particularly useful herein. Examples of other useful alkyl esters include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

7. Alkenyl esters of fatty acids having 10 to 20 carbon atoms. Examples thereof include oleyl myristate, oleyl stearate, and oleyl oleate.

8. Fatty acids having 10 to 20 carbon atoms. Suitable examples include pelargonic, lauric, myristic, palmitic, stearic, isostearic, hydroxystearic, oleic, linoleic, ricinoleic, arachidic, behenic, and erucic acids.

9. Fatty alcohols having 10 to 20 carbon atoms. Lauryl, myristyl, cetyl, hexadecyl, stearyl, isostearyl, hydroxystearyl, oleyl, ricinoleyl, behenyl, erucyl, and 2-octyl dodecanol alcohols are examples of satisfactory fatty alcohols.

10. Fatty alcohol ethers. Ethoxylated fatty alcohols of 10 to 20 carbon atoms include the lauryl, cetyl, stearyl, isostearyl, oleyl, and cholesterol alcohols having attached thereto from 1 to 50 ethylene oxide groups or 1 to 50 propylene oxide groups.

11. Ether-esters such as fatty acid esters of ethoxylated fatty alcohols.

12. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

13. Polyhydric alcohols and polyether derivatives. Propylene glycol, dipropylene glycol, polypropylene glycols 2000, 4000, polyoxyethylene polyoxypropylene glycols, polyoxypropylene polyoxyethylene glycols, glycerol, sorbitol, ethoxylated sorbitol, hydroxypropyl sorbitol, polyethylene glycol 200-6000, methoxy polyethylene glycols 350, 550, 750, 2000, 5000, poly[ethylene oxide] homopolymers (100,000-5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), $C_{15}$-$C_{18}$ vicinal glycol, and polyoxypropylene derivatives of trimethylolpropane are examples of this class of materials.

14. Polyhydric alcohol esters. Ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

15. Wax esters such as beeswax, spermaceti, myristyl myristate, stearyl stearate.

16. Beeswax derivatives, e.g. polyoxyethylene sorbitol beeswax. These are reaction products of beeswax with ethoxylated sorbitol of varying ethylene oxide content, forming a mixture of ether-esters.

17. Vegetable waxes including carnauba and candelilla waxes.

18. Phospholipids such as lecithin and derivatives.

19. Sterols. Cholesterol, cholesterol fatty acid esters are examples thereof.

20. Amides such as fatty acid amides, ethoxylated fatty acid amides, solid fatty acid alkanolamides.

The lotions of this invention can also contain from about 1% to about 10%, preferably from about 2% to about 5%, of an emulsifier. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's *Detergents and Emulsifiers*, North American Edition, pages 317-324 (1986); the disclosures of which are incorporated herein by reference. Preferred emulsifiers are anionic or nonionic, although the other types may also be used. Examples of useful nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene glycol wherein the fatty acid moiety contains from 10 to 20 carbon atoms, fatty acid monoglycerides wherein the fatty acid moiety contains from 10 to 20 carbon atoms, diethylene glycol, polyethylene glycols of molecular weight 200 to 6000, propylene glycol of molecular weight 200 to 3000, sorbitol, sorbitan, polyoxyethylene sorbitol, polyoxyethylene sorbitan and hydrophilic wax esters. Examples of such emulsifiers include polyoxyethylene (8) stearate, myristyl ethoxy (3) myristate, polyoxyethylene (100) monostearate, lauric diethanolamide, stearic monoethanolamide, hydrogenated vegetable glycerides, sodium stearoyl-2-lactylate and calcium stearoyl-2-lactylate.

Suitable anionic emulsifiers include the fatty acid soaps, e.g. sodium, potassium, and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units.

Cationic emulsifiers useful in the present invention include quaternary ammonium, morpholinium and pyridinium compounds. Examples of such emulsifiers include dialkyl ($C_{12}$–$C_{18}$) quaternary ammonium salts, cetyl trimethyl ammonium salts; alkyl dimethyl benzyl ammonium salts, and cetyl pyridinium salts.

The balance of the composition, preferably from about 50% to about 90%, comprises water. The lotions may be formulated by simply admixing all of the components together. Preferably the propoxylated glycerol derivatives are dissolved in the water and the mixture is added to the emollient. Optional components such as the emulsifier or a thickening agent can be added in the composition.

Examples of suitable thickening agents include: cellulose derivatives, (e.g., methyl cellulose and hydroxy propylmethyl cellulose), synthetic high molecular weight polymers (e.g., carboxyvinyl polymer and polyvinyl alcohol), plant hydrocolloids (e.g., karaya gum and tragacanth gum), and clay thickeners (e.g., colloidal magnesium aluminum silicate and bentonite). A more complete disclosure of thickening agents useful herein can be found in Sagarin, *Cosmetics, Science and Technology*, 2nd Edition, Vol. 1 pp. 72–73 (1972), incorporated herein by reference.

B. Skin Conditioning Creams

Skin conditioning compositions of this invention may also be formulated in a cream form. The creams comprise from about 1% to about 60%, preferably from about 3% to about 25%, of the propoxylated glycerol derivatives; from about 1% to about 20%, preferably from about 5% to about 10%, of an emollient; and the balance water, preferably from 50% to about 85%. The emollients described above are also useful in the cream compositions. Optionally, the cream form contains a suitable emulsifier. Emulsifiers described above are useful herein. When an emulsifier is included, it is in the composition at a level of from about 2% to about 10%, preferably from about 2.5% to about 5%.

C. Skin Conditioning Solutions

The compositions of this invention may also be formulated in a solution form. The solutions contain from about 1% to about 60%, preferably from about 2% to about 25%, of the propoxylated glycerol derivatives, and the balance, preferably from about 2% to about 98%, a cosmetically-acceptable organic solvent. The term "cosmetically acceptable organic solvent" refers to an organic solvent that, in addition to being capable of having dispersed or dissolved therein the propoxylated glycerol derivatives, also possesses good cosmetic properties (e.g., does not feel greasy or tacky). Examples of suitable organic solvents are as follows: propylene glycol, polyethylene glycol (200–600) polypropylene glycol (425–2025), glycerol, sorbitol esters, 1,2,6-hexanetriol, ethanol, isopropanol, butanediol, and mixtures thereof. Such organic solvent systems may also contain water, preferably from about 0% to about 90% of the total composition.

These skin conditioning compositions are applied to the skin in the solution form, or the solutions are formulated in an aerosol form and applied to the skin as a spray-on. The skin conditioning compositions in the aerosol form additionally contain from about 3% to about 12%, preferably from about 4% to about 10%, of a suitable propellant. Examples of propellants useful herein include the chlorinated, fluorinated and chlorofluorinated lower molecular weight hydrocarbons. Other propellants useful in the present invention include lower molecular weight hydrocarbon mixtures (e.g., the mixture of butane, isobutane and propane, known commercially as Propellant A46, made by Phillips Chemical Co., a subsidiary of Phillips Petroleum Company), ethers and halohydrocarbons such as dimethyl ether or dichlorodifluoromethane (12) alone or mixtures thereof with dichlorotetrafluoroethane (114). Mixtures of hydrocarbon and halohydrocarbon propellants and nitrous oxide may also be used. Nitrogen and carbon dioxide can also be used as propellant gases. They are used at a level sufficient to expel the contents of the container. A more complete disclosure of propellants useful herein can be found in Sagarin, *Cosmetics Science and Technology*, 2nd Edition, Vol. 2, pp. 443–465 (1972), incorporated herein by reference.

D. Gels and Solid Skin Conditioning Compositions

Skin conditioning solutions of the present invention are formulated into a gel or solid form (e.g., a stick-type composition intended for application to the lips or other parts of the body) by simply admixing with them a sufficient amount of a suitable thickening agent. Examples of suitable thickening agents are described above with respect to the skin conditioning lotions.

E. Optional Components

The skin conditioning compositions of the present invention may contain, in addition to the aforementioned components, a wide variety of additional oil-soluble materials and/or water-soluble materials.

Among the optional oil-soluble materials are nonvolatile silicone fluids such as polydimethyl siloxanes with viscosities ranging from about 10 to about 100,000 centistokes at 25° C. These siloxanes are available from Dow Corning Corporation as the Dow Corning 200 series. These optional oil-soluble materials may comprise up to about 20% of the total composition, preferably up to about 10%.

Various water-soluble materials may also be present in the compositions of this invention. Included are humectants, such as glycerol, sorbitol, propylene glycol, alkoxylated glucose and hexanetriol; thickening agents, such as carboxyvinyl polymers (Carbopols$^R$—sold by B. F. Goodrich Company, such polymers are described in detail in U.S. Pat. No. 2,798,053, July 2, 1957, Brown, incorporated herein by reference); ethyl cellulose, polyvinyl alcohol, carboxymethyl cellulose, vegetable gums and clays such as Veegum$^R$ (magnesium aluminum silicate, R. T. Vanderbilt, Inc.); proteins and polypeptides; preservatives such as the methyl, ethyl, propyl and butyl esters of hydroxybenzoic acid (Parabens—Mallinckrodt Chemical Corporation), EDTA, methylisothiazolinone and imidazolidinyl ureas (Germall 115—Sutton Laboratories); and an alkaline agent such as sodium hydroxide or potassium hydroxide to neutralize, if desired, part of the fatty acids or thickener which may be present. In addition, the skin conditioning compositions herein can contain conventional cosmetic adjuvants, such as dyes, opacifiers (e.g., titanium dioxide), pigments and perfumes.

The skin conditioning compositions herein can also contain topical medicaments such as anti-inflammatory agents, analgesics, anti-infectives, anesthetics, antiseptics, antibacterials, antifungals, antibiotics, astringents, counterirritants, antipuritics, vitamins, anti-oxidants, metal chelators, keratolytic agents (e.g. salicylic acid and urea), agents to increase cell turnover (e.g. allantoin, retinoic acid), cytostatic agents (e.g. selenium sulfide and zinc pyrithione), agents to improve the barrier properties of the skin (e.g. linoleic acid), tanning accelerators (e.g. tyrosine), and natural materials (e.g. aloe vera extract).

The skin conditioning compositions herein can also contain a sunscreen agent. Sunscreen agents particularly useful herein include 2-ethylhexyl p-methoxycinnamate, 4,4'-t-butyl methoxydibenzoylmethane, 2-hydroxy-4-methoxy-benzophenone, octyl dimethyl p-aminobenzoic acid and mixtures thereof. Other sunscreen useful herein include digalloyltrioleate, 2,2-dihydroxy-4-methoxy benzophenone, ethyl 4-[bis(hydroxypropyl)]aminobenzoate, 2-ethylhexyl 2-cyano-3,3-diphenylacrylate, 2-ethylhexyl salicylate, glyceryl p-aminobenzoate, 3,3,5-trimethylcyclohexyl salicylate, methyl anthranilate, p-dimethyl aminobenzoaic, 2-ethylhexyl p-dimethyl amino benzoate, 2-phenylbenzimidazole-5-sulfonic acid, 2-(P-dimethylaminophenyl)-5-sulfonic benzoxazoic acid and mixtures of these compounds. The sunscreen agents disclosed in U.S. Ser. No. 879,724, filed June 27, 1986, Sabatelli, and U.S. Ser. No. 879,725, filed June 27, 1986, Sabatelli and Spirnak, both of which are incorporated herein by reference, are also useful in the present invention.

F. Skin Conditioning Composition Use

The compositions described herein are particularly suited to treating dry skin, particularly the face and hands. An effective amount, from about 0.1 mg/cm$^2$ skin to about 10 mg/cm$^2$ skin, is applied and rubbed into the skin as often as needed for dry skin soothing.

Skin Cleansing Compositions

The skin cleansing compositions of the present invention contain from about 1% to about 60%, preferably from about 2% to about 40%, of the propoxylated glycerol derivatives; and from about 1% to about 90%, preferably 50% to about 85%, of a cosmetically-acceptable surfactant. The term "cosmetically acceptable surfactant" refers to a surfactant which is not only an effective skin cleanser, but also can be used without undue toxicity, irritation, allergic response, and the like.

The physical form of the skin cleansing compositions is not critical. The compositions can be, for example, formulated as toilet bars, liquids, pastes, or mousses. The toilet bar is the most preferred form since this is the form of cleansing agent most commonly used to wash the skin.

A. The Surfactant Component

The surfactant component of the compositions of the present invention can be selected from anionic, nonionic, zwitterionic, amphoteric and ampholytic surfactants, and mixtures of these surfactants. Such surfactants are well-known to those skilled in the detergency art.

The most common type of anionic surfactants can be broadly described as the water-soluble salts, particularly the alkali metal salts, of organic sulfuric reaction products having in the molecular structure an alkyl radical containing from about 8 to about 22 carbon atoms and a radical selected from the group consisting of sulfonic acid and sulfuric acid ester radicals. Important examples of these surfactants are the sodium, ammonium or potassium alkyl sulfates, especially those obtained by sulfating the higher alcohols produced by reducing the glycerides of tallow or coconut oil; sodium or potassium alkyl benzene sulfonates in which the alkyl group contains from about 9 to about 15 carbon atoms, especially those of the types described in U.S. Pat. Nos. 2,220,099 and 2,477,383, incorporated herein by reference; sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid esters of the reaction product of one mole of a higher fatty alcohol (e.g., tallow or coconut oil alcohols) and about three moles of ethylene oxide; sodium or potassium salts of alkyl phenol ethylene oxide ether sulfates with about three moles of ethylene oxide; sodium or potassium salts of alkyl phenol ethylene oxide; sodium or potassium salts of alkyl phenol ethylene oxide ether sulfates with about four units of ethylene oxide per molecule and in which the alkyl radicals contain about 9 carbon atoms; the reaction product of fatty acids esterified with isethionic acid and neutralized with sodium hydroxide where, for example, the fatty acids are derived from coconut oil; sodium or potassium salts of fatty acid amide of a methyl taurine in which the fatty acids, for example, are derived from coconut oil; and others known in the art, such as those specifically set forth in U.S. Pat. Nos. 2,486,921, 2,486,922 and 2,396,278, incorporated herein by reference.

An important type of useful anionic surfactants are soaps. Soaps which can be used as the surfactant in the present compositions include alkali metal (e.g., sodium or potassium) soaps of fatty acids containing from about 8 to about 24, preferably from about 10 to about 20 carbon atoms. The fatty acids used in making the soaps can be obtained from natural sources such as, for instance, plant or animal-derived glycerides (e.g., palm oil, coconut oil, babassu oil, soybean oil, castor oil, tallow, whale oil, fish oil, grease, lard, and mixtures thereof). The fatty acids can also be synthetically prepared (e.g., by oxidation of petroleum stocks or by the Fischer-Tropsch process).

Alkali metal soaps can be made by direct saponification of the fats and oils or by the neutralization of the free fatty acids which are prepared in a separate manufacturing process. Particularly useful are the sodium and potassium salts of the mixtures of fatty acids derived from coconut oil and tallow, i.e., sodium and potassium tallow and coconut soaps.

The term "tallow" as used herein in connection with fatty acid mixtures refers to acids which typically have an approximate carbon chain length distribution of 2.5% $C_{14}$, 29% $C_{16}$, 23% $C_{18}$, 2% palmitoleic, 41.5% oleic and 3% linoleic acid (the first three fatty acids listed are saturated). Other mixtures with similar distribution, such as the fatty acids derived from various animal tallows and lard, are also included within the term tallow. The tallow can also be hardened (i.e., hydrogenated) to convert part or all of the unsaturated fatty acid moieties to saturated fatty acid moieties.

When the term "coconut oil" as used herein refers to fatty acid mixtures which typically have an approximate carbon chain length distribution of about 8% $C_8$, 7% $C_{10}$, 48% $C_{12}$, 17% $C_{14}$, 9% $C_{16}$, 2% $C_{18}$, 7% oleic, and 2% linoleic acid (the first six fatty acids listed being saturated). Other sources having similar carbon chain length distribution, such as palm kernel oil and babassu oil, are included with the term coconut oil.

Nonionic surfactants comprise a class of compounds which may be broadly defined as compounds produced by the condensation of alkylene oxide groups (hydrophilic in nature) with an organic hydrophobic compound, which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

For example, a well-known class of nonionic surfactants is commercially available under the trade name of "Pluronic" marketed by the BASF Wyandotte Corporation. These compounds are formed by condensing ethylene oxide with an hydrophobic base formed by the condensation of propylene oxide with propylene glycol. The hydrophobic portion of the molecule which, of course, exhibits water-insolubility has a molecular weight of from about 1500 to about 1800. The addition of polyoxyethylene radicals to this hydrophobic portion tends to increase the water-solubility of the molecule as a whole and the liquid character of the products is retained up to the point where polyoxyethylene content is about 50% of the total weight of the condensation product.

Other suitable nonionic surfactants include:

(i) The polyethylene oxide condensates of alkyl phenols, e.g., the condensation products of alkyl phenols having an alkyl group containing from about 6 to about 12 carbon atoms in either a straight chain or branched chain configuration, with ethylene oxide, the said ethylene oxide being present in amounts equal to from about 5 to about 25 moles of ethylene oxide per mole of alkyl phenol. The alkyl substituent in such compounds may be derived from polymerized propylene, diisobutylene, octane, and nonane, for example. Examples of compounds of this type include nonyl phenol condensed with about 9.5 moles of ethylene oxide per mole of phenol; dodecyl phenol condensed with about 12 moles of ethylene oxide per mole of phenol; dinonyl phenol condensed with about 15 moles of ethylene oxide per mole of phenol; and diisooctyl phenol condensed with about 15 moles of ethylene oxide per mole of phenol. Commercially available nonionic surfactants of this type include Igepal CO-630, marketed by the GAF Corporation; and Triton X-45, X-114, X-100, and X-102, all marketed by the Rohm & Haas Company.

(ii) Those derived from the condensation of ethylene oxide with the product resulting from the reaction of propylene oxide and ethylene diamine-products which may be varied in composition depending upon the balance between the hydrophobic and hydrophilic elements which is desired. Examples are compounds containing from about 40% to about 80% polyoxyethylene by weight and having a molecular weight of from about 5000 to about 11,000 resulting from the reaction of ethylene oxide groups with a hydrophobic base constituted of the reaction product of ethylene diamine and excess propylene oxide, said base having a molecular weight of the order of 2500 to 3000, are satisfactory. Examples of this type of nonionic surfactant include certain of the commercially available Tetronic compounds, marketed by Wyandotte Chemical Corporation.

(iii) The condensation product of aliphatic alcohols having from 8 to 18 carbon atoms, in either straight or branched chain configuration, with ethylene oxide, e.g., a coconut alcohol ethylene oxide condensate having from 10 to 30 moles of ethylene oxide per mole of coconut alcohol. Examples of commercially available nonionic surfactants of this type include Tergitol 15-S-9 (the condensation product of $C_{11}$–$C_{15}$ secondary alcohol with 9 moles ethylene oxide), marketed by Union Carbide Corporation; Neodol 45-9 (the condensation product of $C_{14}$–$C_{15}$ linear alcohol with 9 moles of ethylene oxide), Neodol 45-7 (the condensation product of $C_{14}$–$C_{15}$ linear alcohol with 7 moles of ethylene oxide), Neodol 45-4 (the condensation product of $C_{14}$–$C_{15}$ linear alcohol with 4 moles of ethylene oxide), marketed by Shell Chemical Company, and Kyro EOB (the condensation product of $C_{13}$–$C_{15}$ linear alcohol with 9 moles ethylene oxide), marketed by The Procter & Gamble Company.

(iv) Trialkyl amine oxides and trialkyl phosphine oxides wherein one alkyl group ranges from 10 to 18 carbon atoms and two alkyl groups range from 1 to 3 carbon atoms; the alkyl groups can contain hydroxy substituents; specific examples are dodecyl di(2-hydroxyethyl)amine oxide and tetradecyl dimethyl phosphine oxide.

Zwitterionic surfactants comprise the betaine and betaine-like compounds wherein the molecule contains both basic and acidic groups which form an inner salt giving the molecule both cationic and anionic hydrophilic groups over a broad range of pH values. Some common examples of these surfactants are described in U.S. Pat. Nos. 2,082,275, 2,702,279 and 2,555,082, incorporated herein by reference. Suitable zwitterionic surfactants have the formula

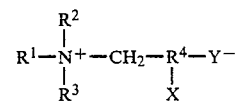

wherein $R^1$ is an alkyl radical containing from about 8 to about 22 carbon atoms, $R^2$ and $R^3$ contain from about 2 to about 3 carbon atoms, $R^4$ is an alkylene chain containing from about 1 to about 3 carbon atoms, X is selected from the group consisting of hydrogen and a hydroxyl radical, Y is selected from the group consisting of carboxyl and sulfonyl radicals and wherein the sum of the $R^1$, $R^2$ and $R^3$ radicals is from about 14 to about 24 carbon atoms.

Amphoteric and ampholytic surfactants which can be either cationic or anionic depending upon the pH of the system are represented by detergents such as dodceyl-beta-alanine, N-alkyltaurines such as the one prepared by reacting dodceylamine with sodium isethionate according to the teaching of U.S. Pat. No. 2,658,072, N-higher alkylaspartic acids such as those produced according to the teaching of U.S. Pat. No. 2,438,091, and the products sold under the trade name "Miranol," and described in U.S. Pat. No. 2,528,378, said patents being incorporated herein by reference.

Additional surfactants useful in the present invention and listings of their commercial sources can be found in McCutcheon's *Detergents and Emulsifiers*, North American Ed. pages 317–324 (1986), incorporated herein by reference.

B. Optional Materials

The compositions of the invention can optionally contain materials which are conventionally used in skin cleansing compositions.

Conventional antibacterial agents and sanitizers can be included in the skin cleansing compositions at levels of from about 0.5% to about 4%. Typical antibacterial sanitizers which are suitable for use herein include 3,4-di- and 3,4',5'-tri-bromosalicylanilides; 4,4'-dichloro-3-(trifluoromethyl)carbanilide; 3,4,4'-trichlorocarbanilide and mixtures of these materials. Use of these and related materials in skin cleansing compositions is described in more detail in Reller, et al., U.S. Pat. No. 3,256,200, issued June 14, 1966, incorporated herein by reference.

Nonionic emollients can be included as skin conditioning agents in the skin cleansing compositions of the present invention at levels up to about 10%. Such materials include for example, mineral oils, paraffin wax having a melting point of from about 100° F. to about 170° F., fatty sorbitan esters (see U.S. Pat. No. 3,988,255, Seiden, issued Oct. 26, 1976, incorporated by reference herein), lanolin and lanolin derivatives, esters such as isopropyl myristate and triglycerides such as coconut oil or hydrogenated tallow.

Free fatty acid, such as coconut oil fatty acid, can be added to the compositions herein at levels up to about 10% to improve the volume and quality (creaminess) of the lather produced by the compositions.

Perfumes, dyes and pigments can also be incorporated into the skin cleansing compositions of the invention at levels up to about 5%. Perfumes are preferably used at levels of from about 0.5% to 3% and dyes and pigments are preferably used at levels of from about 0.001% to about 0.5%.

A particularly preferred optional ingredient is a cationic or nonionic polymeric skin feel aid. Reduced skin irritation benefits of both types of polymers are set out in "Polymer JR for Skin Care" Bulletin, by Union Carbide, 1977. The cationics are preferred over the nonionic because they provide better skin feel benefits. Examples of the cationic polymers and the nonionic polymers useful for this purpose are set out below.

The amount of polymeric skin feel aid found useful in the present invention is from about 0.05% to about 5%, preferably from about 0.1% to about 2%, and more preferably 0.1% to 1.0%.

A particularly preferred skin feel aid is cationic (quaternized) guar gum, e.g., Jaguar C-14-S, from Celanese Corp.

Other types of high molecular weight polymeric skin feel agents, such as nonionic guar gums, Merquats 100 and 550, made by Merck & Co., Inc.; UCARE polymer JR-400, made by Union Carbide Corp.; Mirapol A15 made by Miranol Chemical Company, Inc.; and Galactasol 811, made by Henkel, Inc.; plus others, are usable.

The nonionic polymers found to be useful as skin feel aids include the nonionic polysaccharides, e.g., nonionic hydroxypropyl guar gums, offered by Celanese Water Soluble Polymers, a Division of Celanese Corp. A preferred nonionic hydroxypropyl guar gum material is Jaguar$^R$ HP-60 having hydroxypropyl molar substitution of about 0.6. Another class of useful nonionics is the cellulosic nonionic polymers, e.g., hydroxyethylcellulose and carboxymethylcellulose.

In addition to the aforementioned components, the optional materials listed above with respect to skin conditioning compositions may also be used in the skin cleansing compositions.

C. Preferred Forms of Skin Cleansing Compositions

The compositions of the present invention are preferably prepared in the form of toilet bars, but can also be prepared in other forms such as liquids, pastes or mousses. The toilet bar is the most preferred from since it is the form of cleansing composition most commonly used to wash the skin.

Toilet bars generally comprise from about 50% to about 90% surfactant. Moisture is generally present at levels of from about 5% to about 20%. Liquids generally comprise from about 10% to about 30% surfactant and from about 60% to about 90% water. Pastes generally comprise from about 20% to about 60% surfactant and from about 30% to about 50% water. Pastes and liquids will also generally contain organic thickening agents such as natural gums and polymers.

Examples of soap-based toilet bar compositions are found in U.S. Pat. No. 3,576,749, Megson et al., issued Apr. 27, 1971, incorporated herein by reference. Examples of synthetic-based toilet bars which can be used in preparing compositions of the invention can be found in U.S. Pat. No. 2,987,484, Lundberg et al., issued June 6, 1961, incorporated by reference herein. Other examples of soap/synthetic-based toilet bars can be found in U.S. Pat. No. 3,070,547, Chaffee, issued Dec. 25, 1962 and U.S. Pat. No. 3,376,229, Haas et al., issued Apr. 2, 1968, incorporated herein by reference. Examples of soap-based liquid cleansing compositions which can be used in preparing liquid compositions of the invention are found in U.S. Pat. No. 4,310,433, Stiros, issued Jan. 12, 1982, incorporated herein by reference. Examples of synthetic-based liquid cleansing compositions which can be used in preparing compositions of the invention are found in U.S. Pat. No. 4,338,211, Stiros, issued June 6, 1982, incorporated herein by reference. Paste compositions can be made by appropriate reduction in the levels of water in the compositions of U.S. Pat. Nos. 4,310,433 and 4,338,211.

The skin cleansing compositions of this invention can also be formulated into a pressurized aerosol mousse composition. The mousse composition contains from about 88% to about 97%, preferably from about 90% to about 96%, of a concentrate, and from 2% to about 12% of a propellant. The concentrate comprises from 1% to about 60%, preferably from about 10% to about 50%, of the propoxylated glycerol derivatives and from 3% to about 20%, preferably from about 6% to about 12%, of a soap or a cosmetically-acceptable surfactant.

The cosmetically acceptable surfactants described above are suitable for use in mousse compositions. Preferred surfactants useful in these compositions are described in European Patent Application No. 0194097, Schmidt et al., published Sept. 10, 1986, incorporated herein by reference.

Propellants described above are useful herein. A particularly preferred propellant is a mixture of butane, isobutane, and propane, known commercially as Propellant A46, made by Phillips Chemical Company, a subsidiary of Phillips Petroleum Company.

Although the propoxylated glycerol derivatives of the present invention are particularly suitable for use in skin conditioning/cleansing compositions, they are also suitable for use in detergent compositions which, during use, frequently come in contact with the hands, e.g., compositions for washing hard surfaces, such as counter-tops or floors, or housewares, such as dishes, glasses, pots and pans, etc.

Particularly preferred compositions of the invention are soap-based toilet bars which comprise from about 50% to about 90% soap, from about 1% to about 20% (preferably from about 5% to about 10%) of the propoxylated glycerol derivatives and, optionally, from about 2% to about 10% free fatty acid, preferably coconut oil fatty acid, and from 1% to 20% of an additional anionic surfactant, preferably an alkyl glyceryl ether sulfonate.

D. Skin Cleansing Composition Use

The skin cleansing compositions of the invention are used in the conventional manner, i.e., they are applied to the skin and the skin is rinsed with water or in the case of an emollient mousse composition, the excess composition can be cleanly wiped from the skin (see e.g. Example VII). In the case of liquids and pastes, the composition can be applied "as is" to the skin. In the case of toilet bars, a solution or dispersion of the composition is formed prior to application by wetting the surface of the bar or rubbing the bar onto a wet washcloth. The wet bar or washcloth, which contains a portion of the composition, diluted with water, is then rubbed against the skin.

The following non-limiting examples illustrate the present invention.

EXAMPLE I

Synthesis of a Mixture of 2-Hydroxypropylglyceryl Ether and 1-Hydroxyisopropylglyceryl Ether

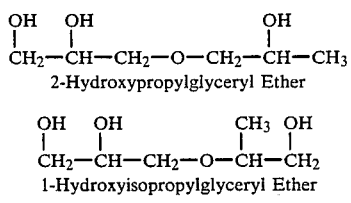

A 2-liter, 3-necked, round-bottom flask equipped with an overhead stirrer, reflux condenser with a dry ice cooled condenser on top, and a dropping funnel was charged with 80% NaH oil dispersion (30.0 g, 1.0 mole). This was washed twice with hexane. Next, 750 mL of solketal was cautiously added (much heat and $H_2$ evolved). After the addition was completed, the amber colored solution was stirred at 80° C. for 1 hour. Next, propylene oxide (52.3 g, 0.90 moles) was added dropwise. After the addition was completed, the temperature of the reaction mixture was raised to 100° C. and stirred for 3 hours. The reaction mixture was then cooled and poured into a separatory funnel containing 700 mL of water and 1 liter of ether. The layers were separated and the aqueous layer extracted with ether (3×500 mL). The combined ether layers were washed with 200 mL of brine, dried over $MgSO_4$, and the solvents removed by rotary evaporation to yield an amber oil. This material was purified by fractional distillation (b.p. 60°–70° C., 0.1 mm) to remove the lower boiling solketal. 84.2 g of the intermediate compound was obtained. This material was dissolved in 200 mL of a 4:1 mixture of ethanol:water. Next, 94.2 g (1 equiv.) of Amberlyst$^R$ 15 cationic exchange resin was added. The mixture was heated with stirring to 60° C. for one hour. The mixture was cooled, filtered through a medium sintered glass funnel, and the resin washed with 200 mL of ethanol. The filtrate was concentrated by rotary evaporation to give a brown oil. This material was purified by Kugel-Rohr distillation (b.p. 100° C., 0.05 mm) to give 57.28 g of a colorless liquid. Analysis: Calculated for $C_6H_{14}O_4$: C, 47.99; H, 9.40; O, 42.61. Found: C, 47.38; H, 9.34; O, 43.39.

EXAMPLE II

Hand and Body Lotion

| Component | Wt. % |
|---|---|
| Distilled Water | 79.26 |
| 2-Hydroxypropylglyceryl Ether | 10.00 |
| Petrolatum | 2.50 |
| Cetyl Alcohol | 1.80 |
| Copolyol[1] - (90% cyclomethicone & 10% Copolyol polymer) | 1.50 |
| Stearyl Alcohol | 1.20 |
| Isopropyl Palmitate | 1.00 |
| Dimethicone[2] | 0.50 |
| Sodium Hydroxide (50%) | 0.34 |
| Stearic Acid | 0.25 |
| Lanolin Acid | 0.25 |
| PEG-100 Stearate | 0.25 |
| Carbomer-934[3] | 0.20 |
| Perfume | 0.20 |
| Methyl Paraben | 0.20 |
| Titanium Dioxide | 0.15 |
| EDTA | 0.10 |
| Propyl Paraben | 0.10 |
| Germall 115[4] | 0.10 |
| Emphos F27-85[5] | 0.10 |
| | 100.00% |

[1]Dow Corning X2-3225C-Cyclomethicone has 5 dimethylsiloxane groups and copolyol polymer has the formula

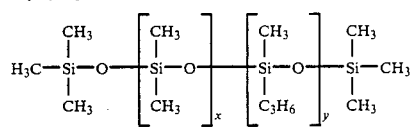

$$O-(CH_2H_4O)_a(C_3H_6O)_bR$$

wherein x and y are selected such that the weight ratio of polydiorgano-siloxane segments to polyoxyalkylene segments is from about 2 to 8 and the mol ratio of a:(a + b) is from about 0.5 to 1.
[2]Dow Corning 200 Fluid.
[3]A carboxy vinyl polymer commercially available from B. F. Goodrich Company.
[4]An imidazolidinyl urea commercially available from Sutton Laboratories.
[5]A glyceride phosphate ester commercially available from Witco Chemical Company.

The above composition is made by adding the following components as described:

| Part | Component |
|---|---|
| I. (Water Phase) | Distilled Water |
| | Carbomer 934 |
| | Sodium Hydroxide |
| | Titanium Dioxide |
| | EDTA |
| II. (Oil Phase) | 2-Hydroxypropylglyceryl ether |
| | Petrolatum |
| | Cetyl Alcohol |
| | Copolyol |
| | Dimethicone |
| | Stearyl Alcohol |
| | Isopropyl Palmitate |
| | Stearic Acid |
| | Lanolin Acid |
| | PEG-100 Stearate |
| | Emphos F-27-85 |
| III. (Preservatives) | Methyl Paraben |
| | Propyl Paraben |
| | Germal 115 |

| Part | Component |
|---|---|
| IV. | Perfume |

The water phase components (Part I) are mixed in a small vessel and heated to 70° C. The oil phase components (Part II) are mixed in a separate mix tank and heated to 70° C. The two mixtures are then poured into a high shear mixer, oil phase first, that is also heated to 70° C. The mixture is blended for 45 seconds at high speed. After the resulting emulsion is cooled to 50° C., the preservatives (Part III) and perfume (Part IV) are added and blended. The composition is finally cooled down to 27°-29° C.

The above skin conditioning composition possesses both excellent skin conditioning and aesthetic properties.

EXAMPLE III

Facial Moisturizing Cream Containing a Sunscreen Agent

| Component | Wt. % |
|---|---|
| Ethylhexyl p-methoxycinnamate | 4.9 |
| Butyl Methoxydibenzoylmethane | 2.1 |
| Ethylene/Acrylate Copolymer[1] | 0.5 |
| 2-Hydroxypropylglyceryl Ether | 5.0 |
| Petrolatum | 2.0 |
| Dimethicone[2] | 0.40 |
| Steareth-100 | 0.70 |
| Glycerol Monostearate | 0.30 |
| Cetyl Alcohol | 1.20 |
| Stearic Acid | 0.52 |
| Carbomer 934[3] | 0.10 |
| Carbomer 941[3] | 0.10 |
| Methyl Paraben[4] | 0.20 |
| Propyl Paraben | 0.10 |
| Imidazolidinyl Urea | 0.10 |
| Tetrasodium EDTA | 0.10 |
| Tyrosine | 0.10 |
| Potassium Hydroxide | 0.37 |
| Titanium Dioxide | 0.40 |
| Perfume | 0.15 |
| Water | 80.66 |
| | 100.00 |

[1] Commercially available from Allied Chemical Company as AC 540A having a weight average molecular weight of 4271
[2] Polydimethylsiloxane available from Dow Corning as DC-200
[3] Carboxyvinyl polymers available from B. F. Goodrich
[4] Preservatives available from Sutton Laboratories The above compositions can be made by adding the following components as described:

| Part | Component |
|---|---|
| I | Water |
| | Carbomer 934 |
| | Carbomer 941 |
| | Methyl Paraben |
| | Propyl Paraben |
| II | 2-Hydroxypropylglyceryl Ether |
| | Butyl Methoxydibenzoylmethane |
| | Cetyl Alcohol |
| | Glyceryl Stearate |
| | Steareth-100 |
| | Stearic Acid |
| | Dimethicone |
| | Petrolatum |
| | Ethylene/Acrylate Copolymer |
| III | Tetrasodium EDTA |
| | Potasium Hydroxide |
| | Titanium Dioxide |
| IV | Tyrosine |
| | Imidazolidinyl Urea |
| | Perfume |

The water phase (Part I) materials are mixed at 71°-99° C. in a scale-mounted mix tank filtered with baffles and an agitator. The oil phase (Part II) is mixed at 71°-110° C. in a separate mix tank fitted with an agitator. Both Part I and Part II are mixed until homogeneous phases are obtained.

The water phase (Part I) is then pumped into the oil phase (Part II) in an amount equal to 60-100% of the oil phase (Part II). This oil/water premix is held at a temperature of from about 71°-99° C. and agitated until a homogeneous mixture is obtained. The oil/water premix is then pumped into the remaining water phase (Part I) and held at a temperature of from about 71°-99° C. Part III ingredients are then added while maintaining agitation and holding the temperature at 71°-99° C. The composition is then passed through a closed vessel equipped with an ultrasonic probe at the flow rate of 0.5-6.5 kg/min. The ultrasonic frequency may range from 15 to 40 kHz. The composition is further processed through a heat exchanger and/or jacket cooling to a temperature of 71°-99° C. The Part IV components are then added while maintaining agitation until a homogeneous mixture is obtained.

The composition is then pumped through a heat exchanger to cool to 21°-32° C. While waiting to reach steady-state operation, the composition is then packed into glass bottles.

This sunscreen composition is easy to apply to the skin, possesses good aesthetics, and the sunscreen agent is not readily rubbed-off. Furthermore, it provides excellent skin conditioning benefits.

EXAMPLE IV

Skin Conditioning Toilet Bar

| Component | Wt. % |
|---|---|
| Tallow/Coconut Soap (50/50) | 66.61 |
| Water | 10.00 |
| 2-Hydroxypropylglyceryl Ether | 4.00 |
| Sodium Coconut Glyceryl Ether Sulfonate | 8.80 |
| Coconut Fatty Acid (CnFA) | 4.00 |
| Perfume | 1.40 |
| NaCl | 1.04 |
| Na$_2$SO$_4$ | 0.34 |
| Na$_4$EDTA | 0.06 |
| TiO$_2$ | 0.20 |
| Jaguar C15 | 1.00 |
| Merquat 550 | 1.00 |
| Minors (Colrants, Preservatives, Fillers, etc.) | 1.55 |
| | 100.00% |

The above composition is prepared in the following manner.

Crutching Step

About 127.6 parts of a mix containing: 29.8% water, 52.7% 50/50 tallow/coconut (T/CN) soap, 16.7% sodium coconut glyceryl ether sulfonate paste, 3.3% coconut free fatty acid (CNFA), 3.1% 2-hydroxypropylglyceryl ether, and 0.2% NaCl are heated to ca. 150°-200° F. (65°-94° C.). About 10.0 parts of the hydrated polymer JAGUAR C-15 are mixed in.

Vacuum Drying Step

The crutcher mix is vacuum dried at ca. 50 mm Hg absolute pressure to reduce the moisture content of the mix to ca. 10% and to plod this soap into noodles. These noodles are passed through a milling step once.

Amalgamating Step

The once-milled soap noodles are weighed and placed in a batch amalgamator. To about 99.1 parts noodles in the amalgamator are added: 0.20 part $TiO_2$, 1.4 parts perfume, 0.15 part colorant solution, 0.15 part of a solution which contains ca. 40% EDTA. The combined ingredients are mixed thoroughly.

Milling Step

Three-roll soap mills are set up with all rolls at 85°–105° F. (29°–41° C.). The mixture from the amalgamator is passed through the mills several times to obtain a homogeneous mix. This is an intimate mixing step.

Plodding and Stamping Steps

A conventional plodder is set up with the barrel temperature at about 90° F. (32° C.) and the nose temperature at about 110° F. (43° C.). The plodder used is a dual stage twin screw plodder that allows for a vacuum of about 40 to 65 mm Hg between the two stages. The soap log extruded from the plodder is typically round or oblong in cross-section, and is cut into individual plugs. These plugs are then stamped on a conventional soap stamping apparatus to yield the finished toilet soap bar.

This is an example of a skin cleansing toilet bar which provides improved skin mildness, while maintaining desirable soap bar properties (e.g. effective skin cleanser and good aesthetics).

EXAMPLE V

Shower/Bath Foam

| Component | Wt. % |
|---|---|
| Sodium Lauryl Ethoxy (3) Sulfate Solution (28.5% solution) | 38.5 |
| Sodium Lauryl Sulfate Solution (28.5% solution) | 31.6 |
| Coconut Monoethanolamide | 4.0 |
| Perfume | 2.0 |
| Ethylene Glycol Distearate | 1.0 |
| Ethylene Diamine Tetraacetic Acid | 0.1 |
| Preservatives | 0.25 |
| Color Solution | 1.1 |
| Citric Acid | 0.12 |
| Hydroxyethyl Cellulose (HEC)[1] | 0.2 |
| Propylene Glycol | 3.0 |
| 2-Hydroxypropylglyceryl Ether | 2.0 |
| Distilled Water | Balance |
| | 100.00% |

[1] Natrosol 250, degree of hydroxyethyl molar substitution = 2.5, supplied by Hercules Incorporated.

The above composition is prepared in the following manner.

A cold (room temperature) mix is prepared by adding ingredients in the following order: 50% of the added distilled water, hydroxyethyl cellulose, sodium lauryl ethoxy (3) sulfate solution and 50% of the sodium lauryl sulfate solution.

A hot (60°–71.1° C., 140°–160° F.) mix is prepared by adding ingredients in the following order: 50% of the added distilled water, 50% of the sodium lauryl sulfate solution, ethylene diamine tetraacetic acid, preservatives, coconut monoethanolamide, propylene glycol and ethylene glycol distearate and 2-Hydroxypropylglyceryl Ether.

The hot mix is poured into the cold mix, with agitation.

The remaining ingredients are mixed in the following order: color solution, citric acid and perfume.

This shower/bath foam is an effective skin cleanser which provides improved skin mildness and good aesthetic properties.

EXAMPLE VI

Facial Cleanser (Lathering Mousse Composition)

| | Wt. % |
|---|---|
| Emulsion Concentrate (A) | |
| DRO Water[1] | 57.63 |
| 2-Hydroxypropylglyceryl Ether | 15.00 |
| Sodium Glyceryl Ether Sulphonate (90% Coconut/10 Tallow) - 50% Active | 12.06 |
| Sodium Lauroyl Sarcosinate - 33% Active | 6.66 |
| PEG 600 | 4.00 |
| Aloe Vera Gel | 1.00 |
| Lexein LP170P (hydrolyzed animal protein) | 1.00 |
| Stearic Acid | 1.00 |
| Citric Acid | 0.30 |
| Jaguar C14-S | 0.25 |
| Anacarado Perfume | 0.20 |
| FD&C Red Dye #4 | 0.20 |
| Lauryl Alcohol | 0.20 |
| Methyl Paraben | 0.20 |
| Germall 115 | 0.10 |
| $Na_4$ EDTA | 0.10 |
| Propyl Paraben | 0.10 |
| | 100.00% |
| A-46 Propellant (Isobutane-Propane) (B) | |
| (6.4 g in 100 g concentrate) | |

[1] Water purified by double reverse osmosis

The composition is prepared in a single batch process. DRO water is brought to 71.1° C. and the Jaguar polymer is added with agitation. Maintaining agitation the following ingredients are added sequentially: AGS, Sodium lauroyl sarcosinate, lauryl alcohol, PEG-600, Parabens, EDTA, dye, 2-Hydroxypropylglyceryl ether, stearic acid, Aloe Vera Gel, and citric acid. The mixture is then cooled to 135–40 degrees F. and the following ingredients are added sequentially with stirring: Lexein, Germall and perfume. The resulting mixture is cooled to room temperature.

The cooled emulsion concentrate is then filled into aluminum cans. Aerosol activator assemblies are then crimped onto the cans to form a tight seal. Pressurized A-46 Propellant is then pumped into the cans in an amount sufficient to provide a composition consisting of 6% propellant and 94% emulsion concentrate in each can.

Upon activation of the aerosol assembly, the composition is dispensed under pressure in the form of a creamy, foaming mousse which can be applied to the skin to effect simultaneous cleansing and conditioning of the skin. Excess composition can be rinsed from the skin.

This is an example of a lathering mousse composition which exhibits excellent skin conditioning properties and aesthetics, and in addition to moisturizing the skin also provides an abundance of rich, creamy foam.

EXAMPLE VII

Facial Cleanser (Emollient Mousse Composition)

| | Wt. % |
|---|---|
| Emulsion Concentrate (A) | |
| Semtol 70 M.O.[1] | 11.00 |
| Cetyl alcohol | 2.40 |
| Ethylhexyloxystearate (Wickhen Chemical Co.) | 2.10 |
| Amerchol L-101[2] | 5.00 |
| Glucamate SSE-20[3] | 3.10 |
| Glucate SS[4] | 1.00 |
| Myristylethoxy (3) palmitate (Scher Chemical Co.) | 1.40 |
| Carbopol 1342[5] | 0.10 |
| 2-Hydroxypropylglyceryl Ether | 7.50 |
| Methyl paraben | 0.20 |
| Propyl paraben | 0.10 |
| Potassium hydroxide (45% in $H_2O$) | 0.20 |
| $Na_4$ EDTA | 0.10 |
| Germall 115 | 0.10 |
| Allantoin | 0.40 |
| FD&C Red #4 (1% in $H_2O$) | 0.20 |
| FD&C Yellow #5 (1% in $H_2O$) | 0.04 |
| Perfume | 0.18 |
| DRO Water[6] | Balance |
| | 100.00 |
| Nitrous Oxide Propellant (B) | |
| (2.1 g in 100 g. concentrate) | |

[1]Mineral Oil (Sonneborn Division of Witco Chemical Co.)
[2]10% solution of lanolin alcohols in mineral oil (Amerchol Corp.)
[3]Condensation product of 20 moles of ethylene oxide with methyl glucoside sesquistearate (Amerchol Corp.) HLB = 15
[4]Methyl glucoside sesquistearate (Amerchol Corp.) HLB = 16
[5]Water-soluble polymeric thickener (B. F. Goodrich Co.)
[6]Water purified by double reverse osmosis The composition is prepared by the following procedure:

A water phase is prepared by mixing the water, Carbopol 1342, 2-Hydroxypropylglyceryl Ether, methyl paraben and propyl paraben together. A separate oil phase is prepared by mixing the mineral oil, cetyl alcohol, ethylhexyloxystearate, Amerchol L-101, myristylethoxy-palmitate, Glucamate SSE-20 and Glucate SS together at 180° F. (82.2° C.). The oil phase is then pumped into the water phase at 160°-210° F. (71.1°-98.9° C.). The potassium hydroxide and $Na_4$ EDTA are then added to this mixture while maintaining the temperature at about 180° F. (82.2° C.). The mixture is then cooled to about 120° F. (49° C.), the Germall 115 is added at about 140° F. (60° C.), the allantoin and FD&C dyes are added at about 125° F. (51.7° C.) and the perfume is added at 120° F. (49° C.). The finished emulsion concentrate is then subjected to continuous mixing while being pumped through a heat exchanger to cool to room temperature.

The cooled emulsion concentrate is then filled into aluminum cans. Aerosol activator assemblies are then crimped onto the cans to form a tight seal. Pressurized nitrous oxide is then pumped into the cans in an amount sufficient to provide a composition consisting of 2% nitrous oxide and 98% emulsion concentrate in each can.

Upon activation of the aerosol assembly, the composition is dispensed under pressure in the form of a creamy, nonfoaming mousse which can be applied to the skin to effect simultaneous cleansing and conditioning of the skin. Excess composition can be cleanly wiped from the skin with no need to rinse.

This is an example of a mild skin cleaning, nonlathering, mousse-forming emulsion which possesses good aesthetics, and leaves the skin after washing, feeling moisturized, soft and smooth.

In Examples II, III, IV, V, VI and VII, substantially similar results are obtained when the 2-Hydroxypropylglyceryl Ether component is replaced, in whole or in part, by an equivalent amount of a propoxylated glycerol derivative represented by the following formulas:

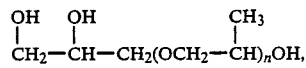

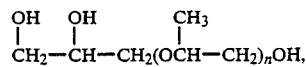

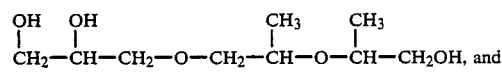

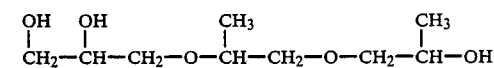

wherein n=1 or 2, or mixtures of these materials.

What is claimed is:

1. A topical skin care composition comprising:
   (a) from about 1% to about 60% by weight of a propoxylated glycerol derivative selected from the group consisting of:

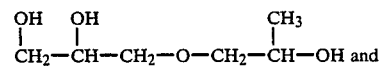

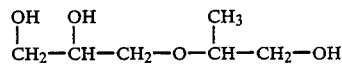

and mixtures thereof; and
   (b) a cosmetically-acceptable topical carrier.

2. A topical skin care composition in the form of a lotion comprising:
   (a) from about 1% to about 60% by weight of a propoxylated glycerol derivative selected from the group consisting of:

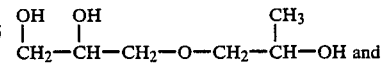

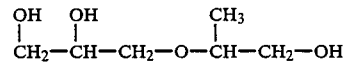

and mixtures thereof;
   (b) from about 1% to about 20% by weight of an emollient selected from the group consisting of hydrocarbon oils and waxes, silicone oils, triglyceride esters, acetoglyceride esters, ethoxylated glycerides, alkyl esters of fatty acids, alkenyl esters of fatty acids, fatty acids, fatty alcohols, fatty alcohol ethers, ether-esters, lanolin and its derivatives, polyhydric alcohols and polyether derivatives, polyhydric alcohol esters, wax esters, beeswax derivatives, vegetable waxes, phospholipids, sterols, amides, and mixtures thereof; and
   (c) from about 50% to about 90% water.

3. The composition of claim 2 wherein the emollient is glycerol.

4. The composition of claim 2 additionally comprising from about 1% to about 10% by weight of an emulsifier.

5. The composition of claim 4 wherein the emulsifier is an organic nonionic surfactant.

6. The composition of claim 2 comprising from about 5% to about 25% of the propoxylated glycerol derivative.

7. A topical skin care composition in the form of a cream comprising:
(a) from about 1% to about 60% by weight of a propoxylated glycerol derivative selected from the group consisting of:

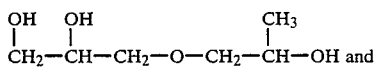

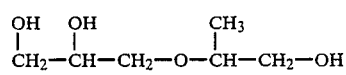

and mixtures thereof;
(b) from about 1% to about 20% by weight of an emollient selected from the group consisting of hydrocarbon oils and waxes, silicone oils, triglyceride esters, acetoglyceride esters, ethoxylated glycerides, alkyl esters of fatty acids, alkenyl esters of fatty acids, fatty acids, fatty alcohols, fatty alcohol ethers, ether-esters, lanolin and its derivatives, polyhydric alcohol esters, wax esters, beeswax derivatives, vegetable waxes, phospholipids, sterols, amides, and mixtures thereof;
(c) from about 2% to about 10% by weight of an emulsifier;
(d) from about 50% to about 85% water.

8. A topical skin care composition in the form of a solution comprising:
(a) from about 1% to about 60% by weight of a propoxylated glycerol derivative selected from the group consisting of:

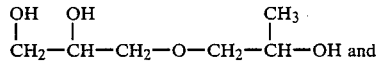

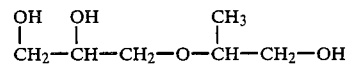

and mixtures thereof;

(b) from about 2% to about 98% of a cosmetically-acceptable organic solvent selected from the group consisting of propylene glycol, polyethylene glycol, polypropylene glycol, glycerine, sorbitol esters, 1,2,6-hexanetriol, ethanol, isopropanol, butanediol, and mixtures thereof; and
(c) from about 0% to about 90% water.

9. The composition of claim 8 additionally comprising from about 3% to about 12% of a propellant material.

10. The composition of claim 8 additionally comprising a thickening agent in an amount sufficient to form a gel.

11. The composition of claim 1 additionally comprising a sunscreen agent.

12. The composition of claim 11 wherein the sunscreen agent is selected from the group consisting of 2-ethylhexyl p-methoxy-cinnamate, 4,4-t-butylmethoxydibenzoylmethane, 2-hydroxy-4-methoxy-benzophenone, octyl dimethyl p-aminobenzoic acid, and mixtures thereof.

13. A topical skin cleansing and conditioning composition comprising:
(a) from about 1% to about 60% by weight of a propoxylated glycerol derivative selected from the group consisting of:

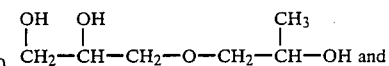

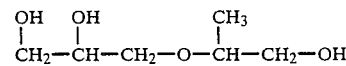

and mixtures thereof; and
(b) from about 1% to about 90% by weight of a surfactant selected from the group consisting of anionic, nonionic, zwitterionic, amphoteric and ampholytic surfactants, and mixtures thereof.

14. The composition of claim 13 wherein the surfactant is anionic and selected from the group consisting of soaps, alkyl glycerol ether sulfonates and mixtures thereof.

15. A method of conditioning skin comprising applying to the skin an effective amount of the composition of claim 1 and rubbing it in.

* * * * *

UNITED STATES PATENT AND TRADEMARK OFFICE
CERTIFICATE OF CORRECTION

PATENT NO. : 4,976,953

DATED : December 11, 1990

INVENTOR(S) : Thomas V. Orr and Anthony D. Sabatelli

It is certified that error appears in the above-identified patent and that said Letters Patent is hereby corrected as shown below:

Column 2, line 21, after "817-820" insert --, 832--.

Column 4, line 53, after "greasiness and/or" insert --stickiness, etc.). A wide variety of cosmetically-acceptable topical--.

Signed and Sealed this

Eighth Day of September, 1992

Attest:

DOUGLAS B. COMER

*Attesting Officer*     *Acting Commissioner of Patents and Trademarks*